United States Patent [19]

Fujinawa et al.

[11] Patent Number: 4,625,053

[45] Date of Patent: Nov. 25, 1986

[54] PROCESS FOR PREPARING OPTICALLY ACTIVE 2-(4-HYDROXY-PHENOXY) PROPIONIC ACID COMPOUNDS

[75] Inventors: Shoji Fujinawa, Narashino; Isao Hashiba, Ichikawa; Kenji Suzuki, Narashino; Syuzi Tsuchiya, Chiba; Yasuo Takakuwa, Funabashi, all of Japan

[73] Assignee: Nissan Chemical Industries Ltd., Tokyo, Japan

[21] Appl. No.: 794,566

[22] Filed: Nov. 6, 1985

[30] Foreign Application Priority Data

Dec. 28, 1984 [JP] Japan .............................. 59-279711

[51] Int. Cl.$^4$ ...................... C07C 51/00; C07C 51/02; C07C 51/347
[52] U.S. Cl. ..................................... 562/401; 560/75; 71/108; 562/478
[58] Field of Search ............................. 562/401, 478

[56] References Cited

FOREIGN PATENT DOCUMENTS 55-092343 7/1980 Japan .

*Primary Examiner*—Natalie Trousof
*Assistant Examiner*—Vera C. Clarke
*Attorney, Agent, or Firm*—Oblon, Fisher, Spivak, McClelland, & Maier

[57] ABSTRACT

A process for preparing an optically active 2-(4-hydroxyphenoxy)propionic acid compound, which comprises reacting an optically active compound having the formula:

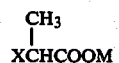

wherein X is a chlorine atom or a bromine atom, and M is a hydrogen atom or an alkali metal atom, with hydroquinone or an alkali metal salt of hydroquinone, in the presence of an alkali metal hydroxide and water, and precipitating optically active disodium 2-(4-hydroxyphenoxy)propionate.

8 Claims, No Drawings

PROCESS FOR PREPARING OPTICALLY ACTIVE 2-(4-HYDROXY-PHENOXY) PROPIONIC ACID COMPOUNDS

The present invention relates to a process for producing optically active 2-(4-hydroxyphenoxy)propionic acid compounds.

2-(4-Hydroxyphenoxy)propionic acid is disclosed in Japanese Unexamined Patent Publication No. 16475/1981 (or UK Patent Publication No. GB 2042539B), Japanese Unexamined Patent Publication No. 22371/1979 or Japanese Unexamined Patent Publication No. 40767/1978, and it is a compound useful as an intermediate for excellent herbicides. More importantly, the herbicides prepared from 2-(4-hydroxyphenoxy)propionic acid as the intermediate, have an asymmetric carbon atom in their structures, and therefore they have two optical isomers. One of the isomers, i.e. the D-form isomer, is known to have a strong herbicidal activity (see e.g. Japanese Unexamined Patent Publication No. 55372/1981). Accordingly, if a herbicide is prepared by using only the optical isomer having the strong herbicidal activity, the necessary dose may be substantially a half as compared with the dose of the racemic modification, which is significant not only from the viewpoints of the environmental protection and conservation of resources, but also from the viewpoint of the industrial advantage that the costs for the production or the application of the herbicide can be reduced.

As a conventional method for the production of optically active 2-(4-hydroxyphenoxy)propionic acid, there is a process disclosed in Japanese Unexamined Patent Publication No. 95237/1984 (hereinafter referred to as "conventional process A"), wherein an optically active α-halopropionic acid and hydroquinone are condensed in an aqueous alkaline solution. On the other hand, as a conventional method for the production of esters of optically active 2-(4-hydroxyphenoxy) propionic acid, there is a process disclosed in published West German patent application No. G.O. DE3150233 (hereinafter referred to as "conventional process B"), wherein an optically active α-halopropionic acid ester and hydroquinone are condensed in the presence of both a DMSO solvent and calcium hydroxide.

As a problem common to the conventional processes A and B, there is a drawback that both of the two hydroxyl groups of hydroquinone are likely to be alkylated to form a by-product in a substantial amount, whereby the yield of the desired product is reduced and the expensive optically active material is thereby unnecessarily wasted. In the above-mentioned patent publication relating to the conventional process A, there is no substantial specific description as to the process and the physical properties of the optically active 2-(4-hydroxyphenoxy) propionic acid, and therefore the results are not known. It has been found by the studies of the present inventors that, when such a reaction is conducted in a homogeneous aqueous solution, the selectivity decreases and a compound of hydroquinone wherein the two hydroxyl groups are alkylated, will be formed as a by-product in a substantial amount. On the other hand, as a process which does not waste the expensive optically active α-halopropionic acid compound, it is conceivable to suppress the conversion and to efficiently recover and recycle hydroquinone for reuse. However, by such a process, the productivity is poor.

Yet, a process wherein water is used as the solvent, is industrially advantageous from the viewpoints of the recovery and reuse of hydroquinone. Thus, the process in which water is used as the solvent and the selectivity is improved is regarded as an extremely good process for producing the optically active 2-(4-hydroxyphenoxy)propionic acid.

In the conventional process B, an expensive optically active material such as optically active n-butyl 2-chloropropionate is used, and nevertheless, it is difficult to avoid partial racemization during the reaction, whereby it is impossible to obtain an optically highly pure alkyl ester of 2-(4-hydroxyphenoxy)propionic acid. Example 3 of G.O. DE3150233 discloses the production of optically active n-butyl 2-(4-hydroxyphenoxy)propionate, wherein the angle of rotation is disclosed to be $[\alpha]_D^{25} + 11.8°$, which clearly indicates racemization having taken place, as compared with the value $[\alpha]_D^{25} + 57.6°$ (neat) of optically active n-butyl 2-(4-hydroxyphenoxy)propionate prepared by the present inventors.

Namely, for the preparation of optically active 2-(4-hydroxyphenoxy)propionic acid compounds, it has been desired, from the technical point of view, firstly to produce an optically highly pure 2-(4-hydroxyphenoxy)propionic acid, and secondly to obtain the mono-substituted product of hydroquinone in good selectivity. It has been required to solve such two problems in order to make the processes industrially applicable.

The present inventors have conducted extensive researches to develop an industrial process for the production of optically active 2-(4-hydroxyphenoxy) propionic acid, and have finally established a process whereby optically highly pure 2-(4-hydroxyphenoxy)propionic acid compounds are obtainable in high selectivity efficiently without using a special apparatus.

Namely, the present invention provides a process for preparing an optically active 2-(4-hydroxyphenoxy)propionic acid compound, which comprises reacting an optically active compound having the formula:

wherein X is a chlorine atom or a bromine atom, and M is a hydrogen atom or an alkali metal atom, with hydroquinone or an alkali metal salt of hydroquinone, in the presence of an alkali metal hydroxide and water, and precipitating optically active disodium 2-(4-hydroxyphenoxy)propionate.

Now, the present invention will be described in detail with reference to the preferred embodiments.

According to conventional techniques disclosed e.g. in patents, the reaction for preparing 2-(4-hydroxyphenoxy)propionic acid and its ester is, in each case, conducted under such a condition that starting materials, desired product and by-products are dissolved. The present inventors have paid a particular attention to the solubility of the starting materials, desired product and by-products, and found that, in the case of the racemic modification, the solubility of disodium 2-(4-hydroxyphenoxy)propionate in water is better than the disodium salt of hydroquinone, whereas, in the case of the optical isomer, the order of the solubility is reversed, and optically active disodium 2-(4-hydroxyphenoxy)propionate is likely to precipitate. This is shown by the following data. In the same manner as will be described in Example 1, racemic sodium α-chloropropionate and sodium L-chloropropionate were reacted, respectively, and the resulting precipitates were filtered, whereupon the wet precipitates and filtrates were analyzed. The results are as follows:

|  | Racemic modification | | | L-form | | |
|---|---|---|---|---|---|---|
|  | HQ | HPA | Di | HQ | HPA | Di |
| Wet Precipitates | 86.8 | 7.8 | 5.4 | 21 | 76.4 | 2.6 |
| Filtrates | 32.4 | 55.3 | 12.4 | 73.3 | 19.8 | 6.9 |

(Unit: mole %)
HR: Disodium salt of hydroquinone
HPA: Disodium 2-(4-hydroxyphenoxy)propionate
Di: Di-substituted product of hydroquinone By utilizing such a nature, the formed optically active disodium 2-(4-hydroxyphenoxy)propionate is withdrawn out of the reaction system in the form of solid, whereby it is possible to successfully suppress the formation of the by-product i.e. a di-substituted product of hydroquinone and to substantially improve the selectivity for the desired product.

Specifically, an alkali metal salt of an optically active α-halopropionic acid is reacted with hydroquinone or an alkali metal salt of hydroquinone, in the presence of an alkali metal hydroxide and a proper amount of water, while optically active disodium 2-(4-hydroxyphenoxy)-propionate is permitted to precipitate, whereby an optically highly pure 2-(4-hydroxyphenoxy)propionic acid compound is obtainable in good selectivity.

The alkali metal salt of an optically active α-halopropionic acid can be prepared from optically active α-halopropionic acid esters. Namely, it is possible to obtain the alkali metal salt of an optically active α-halopropionic acid without impairing the optical purity, by adding optically active α-halopropionic acid esters to an aqueous alkali metal solution and hydrolyzing it, followed by the distilling off of water for isolation. The alkali metal salt of an optically active α-halopropionic acid may be used in a solid form, or in the form of an aqueous solution. It is preferred to remove the alcohol constituting an ester since the inclusion of such an alcohol reduces the selectivity. Further, it is preferred that the alkali metal salt of an optically active α-halopropionic acid is added gradually rather than all at once in order to adequately precipitate the optically active disodium 2-(4-hydroxyphenoxy)propionate.

As X in the formula I, there may be employed a chlorine atom and a bromine atom. The chlorine atom is most preferred from the economical viewpoint. When an alkali metal salt is to be prepared by using an ester, a lower alkyl group is employed as the ester moiety, and the smaller the number of carbon atoms of the ester moiety, the better the optical purity. The reaction scheme is shown as follows:

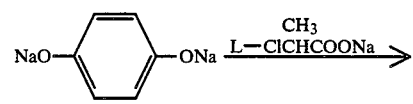

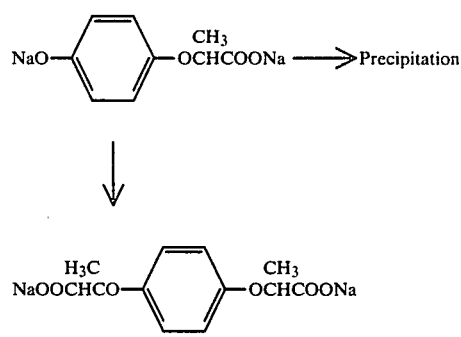

As is apparent from the reaction scheme, it is important to employ such conditions that the optically active disodium 2-(4-hydroxyphenoxy)propionate precipitates while the reaction is conducted. Accordingly, the amount of water, the temperature, the salt for salting out, etc. are influential to one another. Water is used in an amount from 1 to 2.5 times by weight the amount of hydroquinone. The reaction temperature is preferably from 20° to 80° C., most preferably from 20° to 50° C. As the salt for salting out, there may be employed a salt which is soluble in water, such as an alkali metal hydroxide, sodium chloride and sodium sulfate. These conditions may suitably be determined depending upon the particular operation for production.

The alkali metal hydroxide to be used for condensation may be, for instance, lithium hydroxide, sodium hydroxide or potassium hydroxide. From the viewpoints of economy and selectivity, sodium hydroxide is most preferred. The base is used usually in an amount of from 1.5 to 10 mols, most preferably from 1.5 to 4 mols, relative to one mol of hydroquinone. The optically active 2-(4-hydroxyphenoxy)propionic acid compound prepared by this process, has substantially the same optical purity as that of the optically active starting sodium α-halopropionate.

The obtained optically active 2-(4-hydroxyphenoxy)-propionic acid can be converted to a desired alkyl ester by azeotropically dehydrating it with the corresponding alcohol (e.g. methanol, ethanol or n-butanol) in an aromatic hydrocarbon solvent such as benzene or in an ether solvent such as n-butyl ether in the presence of an acid catalyst such as hydrochloric acid, sulfuric acid or p-toluenesulfonic acid, for an ester-forming condensation reaction. During the esterification, no substantial racemization takes place, and the steric structure is thereby maintained. As the alcohol for this purpose, it is practical to use a lower alkyl alcohol such as methanol, ethanol or n-butanol. However, the alcohol is not restricted to these specific examples. For instance, an alkoxy alcohol, a cycloalkyl alcohol or an alkenyl alcohol may also be employed for the reaction.

By the development of a process for producing an optically active 2-(4-hydroxyphenoxy)propionic acid or its ester in high selectivity and with a high optical purity by reacting an optically active chloropropionic acid ester or an optically active chloropropionic acid alkali metal salt with hydroquinone or its alkali metal salt, it has now become possible to produce an alkyl ester of a 2-(4-heteroalkyloxyphenoxy)propionic acid as an active ingredient of excellent herbicides, in an industrially advantageous manner.

Now, the present invention will be described in detail with reference to Examples and a Reference Example. However, it should be understood that the present invention is by no means restricted by these specific Examples.

EXAMPLE 1

98 g of methyl L-α-chloropropionate was dropwise added to an aqueous solution comprising 35.2 g of sodium hydroxide and 150 g of water at a temperature of from 20° to 40° C. After the dropwise addition, 90 g of the mixture of formed methanol and water was distilled off under reduced pressure at a temperature of not higher than 45° C., whereby an aqueous solution of sodium L-α-chloropropionate was obtained. This aqueous solution was dropwise added to a mixture comprising 96 g of sodium hydroxide, 137 g of water and 110 g of hydroquinone, in a nitrogen atmosphere over a period of 3 hours. After the dropwise addition, the mixture was reacted at 40° C. for 5 hours. 177 g of 35% hydrochloric acid was added thereto, and then 362 g of methylisobutylketone, 147 g of water and 10 g of sodium hydrogencarbonate were added. The mixture was subjected to liquid separation. The aqueous layer was further acidified with 35% hydrochloric acid and D-2-(4-hydroxyphenoxy)propionic acid was extracted with methylisobutylketone, and then methylisobutylketone was distilled off from the organic layer under reduced pressure. After an addition of ethanol, the solution was subjected to esterification in the presence of sulfuric acid as a catalyst, followed by fractional distillation, whereby 147 g of ethyl D-2-(4-hydroxyphenoxy)propionate was obtained. The optical purity was measured by liquid chromatography and found to be 93% e.e. 12.4 g of a di-substituted substance was obtained as the later fraction.

EXAMPLE 2

To a mixture comprising 11 g of hydroquinone, 14 g of water and 8.8 g of sodium hydroxide, 10.4 g of sodium L-α-chloropropionate was added over a period of 3 hours while maintaining the mixture at a level of 40° C. Thereafter, the mixture was stirred at 40° C. for 5 hours and stirred at 60° C. for further 1 hour. The reaction solution was adjusted to a pH of 1 with hydrochloric acid, and extracted twice with 100 g of methylisobutylketone. The organic layer was sampled and esterified with diazomethane, and then quantitatively analyzed by gas chromatography. 13.8 g of methyl D-2-(4-hydroxyphenoxy)propionate was detected. The optical purity was measured by liquid chromatography and found to be 94% e.e. 0.8 g of a di-substituted substance was detected.

EXAMPLE 3

136.5 g of ethyl L-α-chloropropionate was dropwise added to an aqueous solution comprising 40 g of sodium hydroxide and 150 g of water at a temperature of from 20 to 40° C. After the dropwise addition, 110 g of the mixture of formed ethanol and water was distilled off under reduced pressure at a temperature of not higher than 45° C., whereby an aqueous solution of sodium L-α-chloropropionate was obtained. This aqueous solution was dropwise added to a mixture comprising 96 g of sodium hydroxide, 150 g of water and 110 g of hydroquinone in a nitrogen atmosphere over a period of 3 hours. After the dropwise addition, the mixture was reacted at 40° C. for 5 hours, and 50° C. for further 1 hour. 146 g of 35% hydrochloric acid was added thereto, then 362 g of methylisobutylketone, 147 g of water and 10 g of sodium hydrogencarbonate were added, and then the mixture was subjected to liquid separation. The aqueous layer was further acidified with 35% hydrochloric acid and D-2-(4-hydroxyphenoxy)propionic acid was extracted with methylisobutylketone, and then methylisobutylketone was distilled off from the organic layer under reduced pressure. After an addition of ethanol, the solution was subjected to esterification in the presence of sulfuric acid as a catalyst, followed by fractional distillation, whereby 168 g of ethyl D-2-(4-hydroxyphenoxy)propionate was obtained. The optical purity was measured by liquid chromatography and found to be 93% e.e. 29.4 g of a di-substituted substance was detected from the later fraction and the bottom residue.

EXAMPLE 4

To a mixture comprising 11 g of hydroquinone, 22 g of water, 8.8 g of sodium hydroxide and 2 g of sodium chloride, 10.4 g of sodium L-α-chloropropionate was added over a period of 3 hours while maintaining the mixture at a level of 40° C. Thereafter, the mixture was stirred at 40° C. for 5 hours and stirred at 60° C. for further 1 hour. The reaction solution was adjusted to a pH of 1 with hydrochloric acid, and extracted twice with 100 g of methylisobutylketone. The organic layer was sampled and esterified with diazomethane and then quantitatively analyzed by gas chromatography, whereby 13.3 g of methyl D-2-(4-hydroxyphenoxy)propionate was detected. The optical purity was measured by liquid chromatography and found to be 94% e.e. 1.0 g of a di-substituted substance was detected.

REFERENCE EXAMPLE 3.98 g of 2,6-dichloroquinoxaline, 4.33 g of ethyl D-2-(4-hydroxylphenoxy)propionate [$[\alpha]_D^{25}$+42.5° (C=1.14, chloroform), optical purity: 93% e.e.], 2.76 g of potassium carbonate and 19.9 g of acetonitrile were mixed. The mixture was refluxed for 6 hours under stirring, and then the solvent was distilled off under reduced pressure. To the residue, 100 ml of toluene and 50 ml of water were added for extraction. The toluene layer was taken, and washed twice with 50 ml of water, and then the solvent was distilled off, whereby 7.55 g of slightly yellow solid was obtained. This solid was recrystallized from 11.9 g of ethanol, whereby 6.45 g of ethyl D-2-[4-(6-chloro-2-quinoxalinyloxy)phenoxy]propionate was obtained as colorelss crystals.

Yield: 87%

The optical purity by the NMR analysis using a shift reagent was 93% e.e.

We claim;

1. A process for preparing an optically active 2-(4-hydroxyphenoxy)propionic acid compound, which comprises reacting an optically active compound having the formula:

wherein X is a chlorine atom or a bromine atom, and M is a hydrogen atom or an alkali metal atom, with hydroquinone or an alkali metal salt of hydroquinone, in the presence of an alkali metal hydroxide and water, and precipitating an optically active di-alkali-meter 2-(4-hydroxyphenoxy)propionate.

2. The process according to claim 1, wherein the amount of water is from 1.0 to 2.5 times by weight the amount of hydroquinone.

3. The process according to claim 2, wherein the reaction temperature is from 20° to 80° C.

4. The process according to claim 1, wherein X in the formula I is a chlorine atom.

5. The process according to claim 1, wherein X in the formula I is a chlorine atom, and M in the formula I is a sodium atom.

6. The process according to claim 1, wherein said alkali metal is sodium.

7. The process according to claim 3, wherein the reaction temperature is from 20°–50° C.

8. The process according to claim 1, wherein said alkali metal hydroxide is used in the amount of from 1.5 to 10 moles per mole of hydroquinone.

* * * * *

UNITED STATES PATENT AND TRADEMARK OFFICE
CERTIFICATE OF CORRECTION

PATENT NO. : 4,625,053

DATED : November 25, 1986

INVENTOR(S) : Shoji Fujinawa et al

It is certified that error appears in the above-identified patent and that said Letters Patent is hereby corrected as shown below:   Title page:

In the Abstract, line 1, and line 2, change "2-(4-hydroxy-phenoxy)propionic" to read -- 2-(4-hydroxyphenoxy)propionic--.

Column 1, line 41, change "patent application" to read --Patent Application--.

Column 3, in the footnote to the table, change "HR" to read --HQ--.

Column 6, line 51, change "colorelss" to read --colorless--.

Column 7, line 1, change "meter" to read --metal--.

Signed and Sealed this

Thirty-first Day of May, 1988

Attest:

DONALD J. QUIGG

Attesting Officer

Commissioner of Patents and Trademarks